United States Patent [19]

Hwang

[11] Patent Number: 5,293,117
[45] Date of Patent: Mar. 8, 1994

[54] MAGNETIC FLAW DETECTOR FOR USE WITH FERROMAGNETIC SMALL DIAMETER TUBULAR GOODS USING A SECOND MAGNETIC FIELD TO CONFINE A FIRST MAGNETIC FIELD

[75] Inventor: Jackson H. Hwang, Houston, Tex.

[73] Assignee: Western Atlas International, Inc., Houston, Tex.

[21] Appl. No.: 882,810

[22] Filed: May 14, 1992

[51] Int. Cl.[5] ............ G01N 27/72; G01N 27/82; G01R 33/12
[52] U.S. Cl. .................. 324/220; 324/232; 324/242
[58] Field of Search ............ 324/219, 220, 221, 227, 324/232, 242

[56] References Cited

U.S. PATENT DOCUMENTS

| | | | |
|---|---|---|---|
| 3,091,733 | 5/1963 | Fearon et al. | 324/220 |
| 4,088,946 | 5/1978 | Charles et al. | 324/220 |
| 4,447,777 | 5/1984 | Sharp et al. | 324/220 |
| 4,602,212 | 7/1986 | Hiroshima et al. | 324/227 |
| 4,789,827 | 12/1988 | Bergander | 324/220 |

OTHER PUBLICATIONS

Full Signature Multiple-Channel Vertilog, G. W. Adams et al., Society of Petroleum Engineers, May 1991.

Primary Examiner—Walter E. Snow
Attorney, Agent, or Firm—William A. Knox

[57] ABSTRACT

A magnetic flaw detector for use in small-diameter tubular goods employs a second magnetic field to confine a first magnetic field to reside within a desired volumetric region in the wall of a specimen under test. A flux leakage detector and a variable reluctance sensor provide means for detecting and discriminating between defects on the inner and outer surfaces of the specimen.

6 Claims, 3 Drawing Sheets

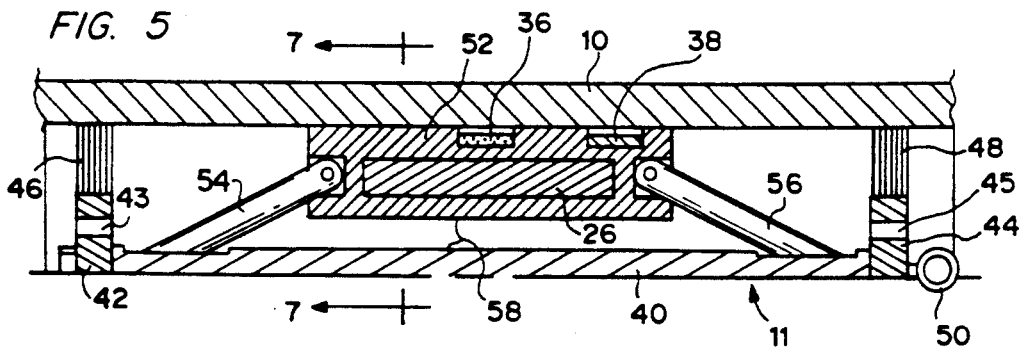
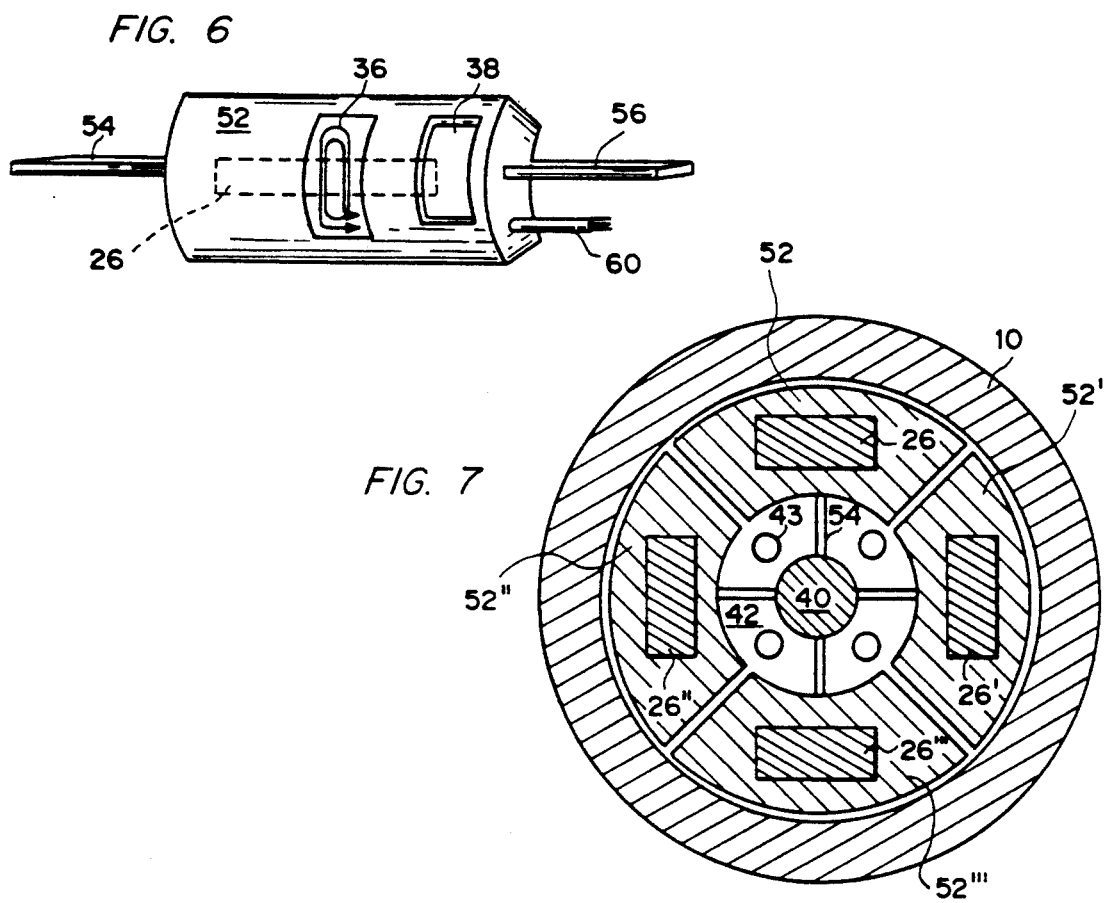
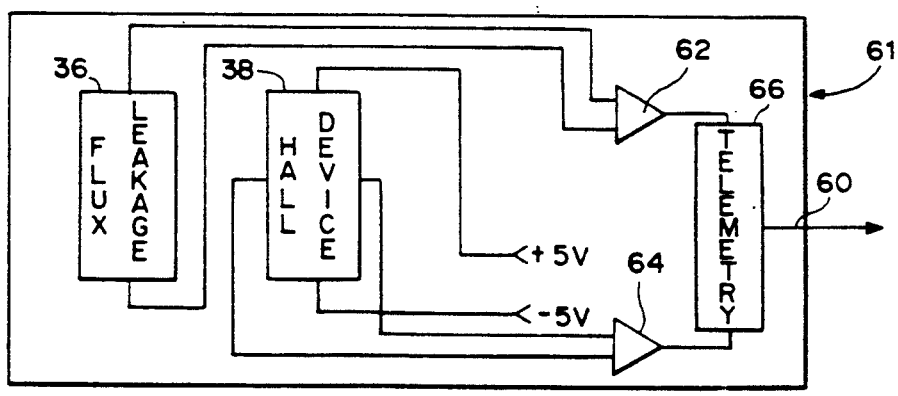

MAGNETIC FLAW DETECTOR FOR USE WITH FERROMAGNETIC SMALL DIAMETER TUBULAR GOODS USING A SECOND MAGNETIC FIELD TO CONFINE A FIRST MAGNETIC FIELD

BACKGROUND OF THE INVENTION

1. Field of the Invention

Herein is disclosed a magnetic flux inspection probe for detecting internal and external flaws in tubular goods. The probe employs a dual-path magnetic field wherein a second magnetic field is used to constrain a first magnetic field to remain within a specified volumetric region of a specimen under inspection. By use of the disclosed system, the physical size of the magnetic probe can be substantially reduced making the device practical for use in small-diameter tubing.

2. Discussion of the Prior Art

Flaws in ferromagnetic material and in particular, in tubular goods such as, for example, pipes and well casing, are commonly detected by establishing a magnetic field in the wall thereof. For simplicity, the term "pipe" will be deemed to include all forms of tubular goods, including structural shapes having an infinite radius of curvature. Distortion of the magnetic field caused by pits, corrosion and changes in the structure of the specimen such as might be caused by couplings, welds or collars, may be found by eddy-current and flux leakage detectors. Hall effect devices may be used to detect changes in the wall thickness.

Typically, a magnetic probe consists of an elongated magnet that has enlarged pole pieces on each end. The pole pieces are separated from the inner pipe wall by a small clearance. The magnet may be a DC-energized electromagnet or it may be a permanent magnet. The respective sensors may be radially arranged around the magnet core, in close contact with the inner pipe surface or they may be supported on flexibly-mounted shoes that are pressed against the interior wall. As the probe is drawn past a pipe defect, changes in the magnetic flux pattern induce a corresponding transient voltage in the sensors. The transient voltage may be recorded on an oscillograph or other recording medium as a voltage level plotted as a function of linear position of the probe along the specimen.

There are a number of magnetic probes that are available. For example, U.S. Pat. No. 4,789,827, issued Dec. 6, 1988 to Bergander discloses a magnetic flux detection probe that includes first and second flux leakage sensing coils mounted within the probe housing. Sensing coils, radially offset with respect to each other provide a measure of the flux leakage to detect flaws in the pipe under inspection. A Hall effect device senses variations of the pipe thickness.

U.S. Pat. No. 4,088,946 issued May 9, 1978 teaches a magnetic inspection tool that uses a central magnetizer and a Hall effect sensor. Means are provided for nulling out the magnetic field of the main magnetizer so that the Hall effect device will be more sensitive to small flux changes due to pits and corrosion in the piping.

U.S. Pat. No. 4,447,777 issued May 8, 1984 to M. R. G. Sharp et al. teaches a pipeline inspection vehicle which includes a central magnetizer having pole pieces that consist of ferromagnetic wire-brush segments to close the magnetic circuit through the pipe. The brushes rub against the interior pipe wall and also serve as centralizers for the probe. The flux sensor coils are carried on a plurality of shoes, distributed radially around the tool. The sensor shoes are spring-loaded so as to press against the inner pipe wall.

A DC magnetic inspection device for use in cased boreholes is described in a paper presented to the Society of Petroleum Engineers, May, 1991 entitled *Full Signature Multiple-Channel Vertilog*, by G. W. Adams et al. This device employs a poled electromagnet and associated sense coils for detecting flux leakage and eddy currents caused by pipe defects. The data-gathering system of this tool employs digital technology.

The design of a magnetic probe requires that the cross sectional areas of the pole pieces be larger than the cross sectional area of the tubing. If that is not true, the pipe will be magnetically under saturated. Ideally, the entire magnetic field would be confined to a closed circuit, through the pipe wall, between the pole pieces. In actual fact, there are significant losses in field strength due to open-ended stray fields emanating outwardly from the ends of the magnet. For that reason, the magnetizer element must be relatively large volumetrically to provide a sufficiently strong magnetic field for useful inspection purposes.

In relatively large pipes, exceeding four or five inches in diameter, there is adequate space inside the pipe to accommodate a magnetizer having the required physical size. For small tubing on the order of 2.375" to 3.5" there is simply not enough room for a magnetizer of the necessary cross-sectional area. There is a need therefore for a magnetic flaw detector that can be used in small diameter tubing as well as in tubing of larger diameters.

SUMMARY OF THE INVENTION

This invention provides a magnetic inspection probe for use with ferromagnetic material. In this tool, a dual-element magnetizer is provided. A first magnetizer having pole pieces of opposite polarity establishes a first magnetic field circuit through the wall of a ferromagnetic specimen to be examined. A second magnetizer having pole pieces of opposite polarity, provides a magnetic field that confines the first magnetic field to a desired volumetric region in the wall of the specimen under study, thereby to increase the magnetic flux density within that region. A flux leakage sensor detects defects in the material of the specimen that give rise to distortions in the magnetic field. A variable reluctance sensor detects defects in the material that create variations in the reluctance of the first magnetic field circuit.

In a preferred embodiment, the first magnetizer is positioned between the pole pieces of the second magnetizer. The first magnetizer is oriented such that poles of like polarity of the first and second magnetizers are juxtapositioned.

In an embodiment for use in ferromagnetic tubular goods having a small radius of curvature, the first magnetizer, the flux leakage sensor and the variable reluctance sensor are mounted in a shoe that is flexibly supported from the second magnetizer between the pole pieces thereof. Resilient means press the shoe against the interior wall of the tubular goods. Output signals provided by the flux leakage sensor and the variable reluctance sensor provide means for discriminating between defects that are internal to the tubular goods and defects that are exterior thereto.

In another embodiment of this invention, the second magnetizer consists of an elongated permanently-magnetized core that is terminated at each end by a vented ferromagnetic prehensile pole piece. A plurality of radially-disposed shoes are flexibly supported around the core of the second magnetizer between the prehensile pole pieces on each end of the magnetized core. Each shoe includes a magnetic element that functions as a first magnetizer for that shoe. Included also in the shoe are a flux leakage sensor and a variable reluctance sensor.

BRIEF DESCRIPTION OF THE DRAWINGS

These and other benefits and advantages of this invention will be better understood by reference to the appended detailed description and the drawings wherein:

FIG. 5 is a cross section along the length of one embodiment of the magnetic probe of this invention;

FIG. 6 is an isometric view of one shoe of the probe of FIG. 5;

FIG. 7 is a cross section along line 7—7 of FIG. 5;

FIG. 8 is a schematic diagram of the sensor electronics.

DETAILED DESCRIPTION OF THE PREFERRED EMBODIMENT

Figure 1:
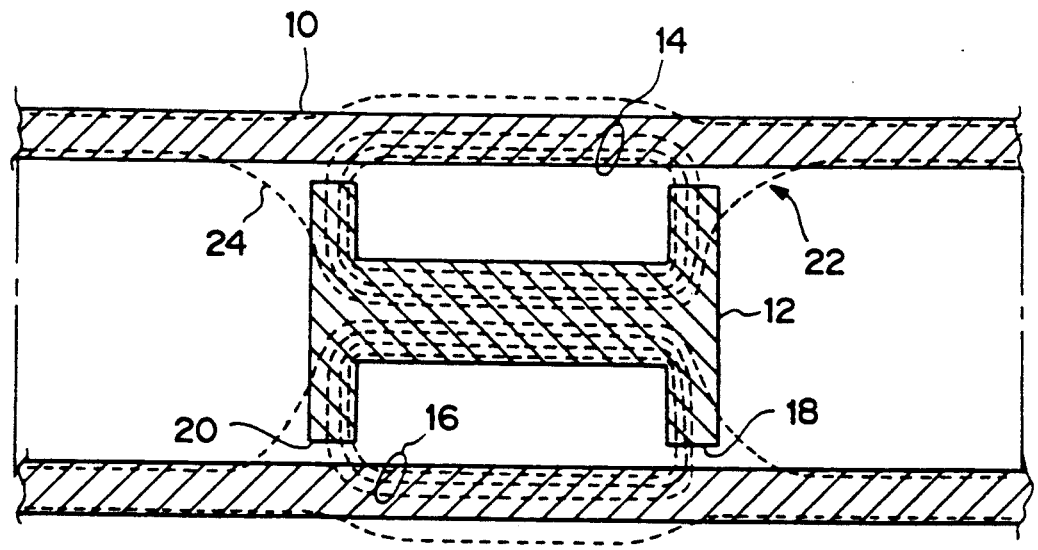
FIG. 1 represents the flux pattern of a conventional magnetic probe as applied to tubular goods.

In FIG. 1, there is shown a pipe specimen 10 in which is positioned a cylindrical magnetizer element 12 that may be a permanent magnet. The magnetic lines of force, shown by the sets of dashed lines 14 and 16, form a magnetic circuit through the body of the magnetizer 12, out from the pole pieces 18 and 20, which have opposite polarity, and through the wall of the specimen 10. Ideally, the entire magnetic field would form a closed circuit through the wall of the specimen between the pole pieces 18 and 20. But stray fields of considerable magnitude such as 22 and 24 emanate from the ends of the magnetizer outwardly, thereby substantially attenuating the useful flux density between the poles. The area of the pole faces of the magnetizer must be made quite large to make up for the flux density loss due to stray fields. As pointed out earlier, in tubular goods having small diameter (defined as a diameter less than 4.5"), lack of space limits the physical size of a magnetic inspection probe.

Figure 2:
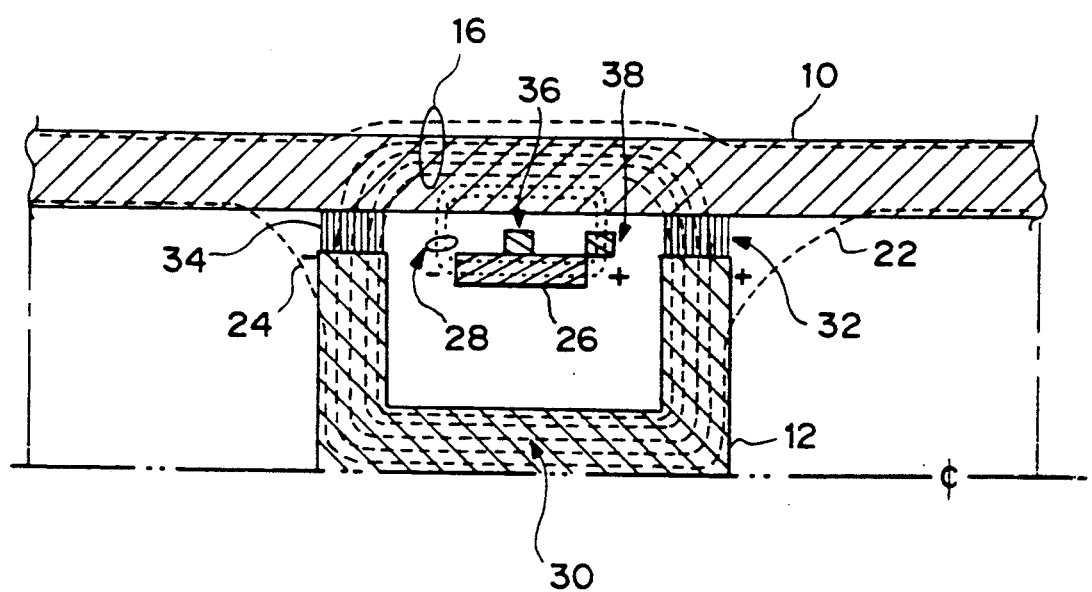
FIG. 2 is a schematic showing of the arrangement of the essential components of this invention.

In FIG. 2, a dual magnetizer configuration is shown. A first magnetizer 26, which preferably is a permanent magnet, having poles of opposite polarity, is positioned between the pole pieces of a second magnetizer 12, which also preferably is a permanent magnet. The magnetic flux lines of the first magnetizer are shown as 28 (dotted lines) which form a circuit through wall 10 between the poles of magnetizer 26. It is to be observed that like poles (+ and −) of the first and second magnetizers are positioned next to each other. The magnetic flux lines 30 (dashed lines) of second magnetizer 12 form a circuit through prehensile pole pieces 32 and 34 and the pipe wall 10. Since the magnetic fields 28 and 30 are of the same polarity, the magnetic field due to second magnetizer 12, being stronger, repels the magnetic field due to first magnetizer 26 and effectively confines that field to a desired volumetric region of the wall 10 of the specimen under study. In effect, the second magnetizer encloses the magnetic field of the first magnetizer in a magnetic bottle. In a preferred arrangement, the field strength of the first magnetizer is 2-3 kG and that of second magnetizer is about 10 kG. By the above stratagem, loss of flux density due to stray fields is eliminated and use of magnetizers of smaller physical size and diameter becomes possible. Since permanent magnets are used, the bulky coils, needed for an electromagnet, are absent.

As is well-known, in an intact specimen, the magnetic field resident therein is uniform. Around a pit or defect, the field is disturbed and lines of magnetic flux bulge out of the specimen wall to form a magnetic pimple in the otherwise uniform field. The rate of change of the leakage flux-density along the axis of the specimen is related to the loss or gain of the metal within the region of the disturbance. A sense coil passing the disturbed region will develop an output voltage of a magnitude that reflects the rate of change of the leakage flux-density vector.

Associated with first magnetizer 26 are flux leakage sensor 36 and variable reluctance sensor 38. Flux leakage sensor 36 may be an elongated wire coil arranged orthogonally to the axis of magnet element 26. As explained above, an electrical voltage is induced in the coil when the inspection probe, including the coil, is moved past a defect or pit on either the inside or outside of the specimen.

The variable reluctance sensor 38 is a well-known Hall effect device. It responds to a change in the reluctance of the magnetic circuit such as when the sensor passes over a pit on the interior surface of the specimen. As shown in FIG. 2, the flux leakage sensor is mounted over the center of the first magnetizer 26. The variable-reluctance sensor is mounted at the end of magnetizer 26 as a part of the magnetic circuit. It senses the change in reluctance due to a change in the length of the gap between sensor and specimen wall in the presence of a pit. Thus, the flux leakage sensor responds to defects on either side of the specimen. The variable reluctance sensor responds only to defects on the side of the specimen facing the probe.

Figure 3:
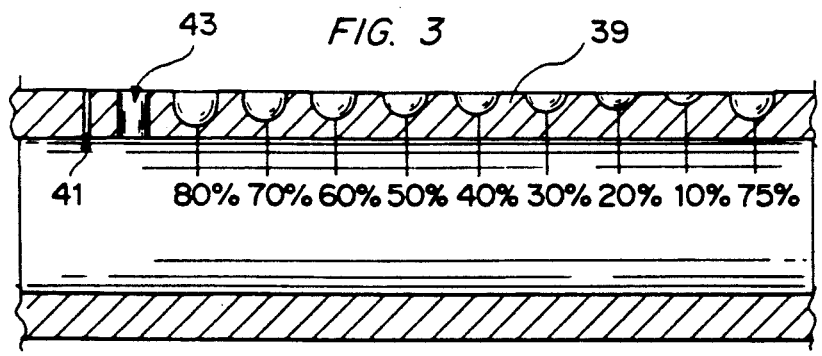
FIG. 3 is a pipe specimen having internal and external defects.

FIG. 3 illustrates a test specimen of pipe 39 that has nine exterior pits having depths ranging from 10% to 80% of the wall thickness. Two through-holes 41 and 43 of different sizes represent internal defects.

Figure 4:
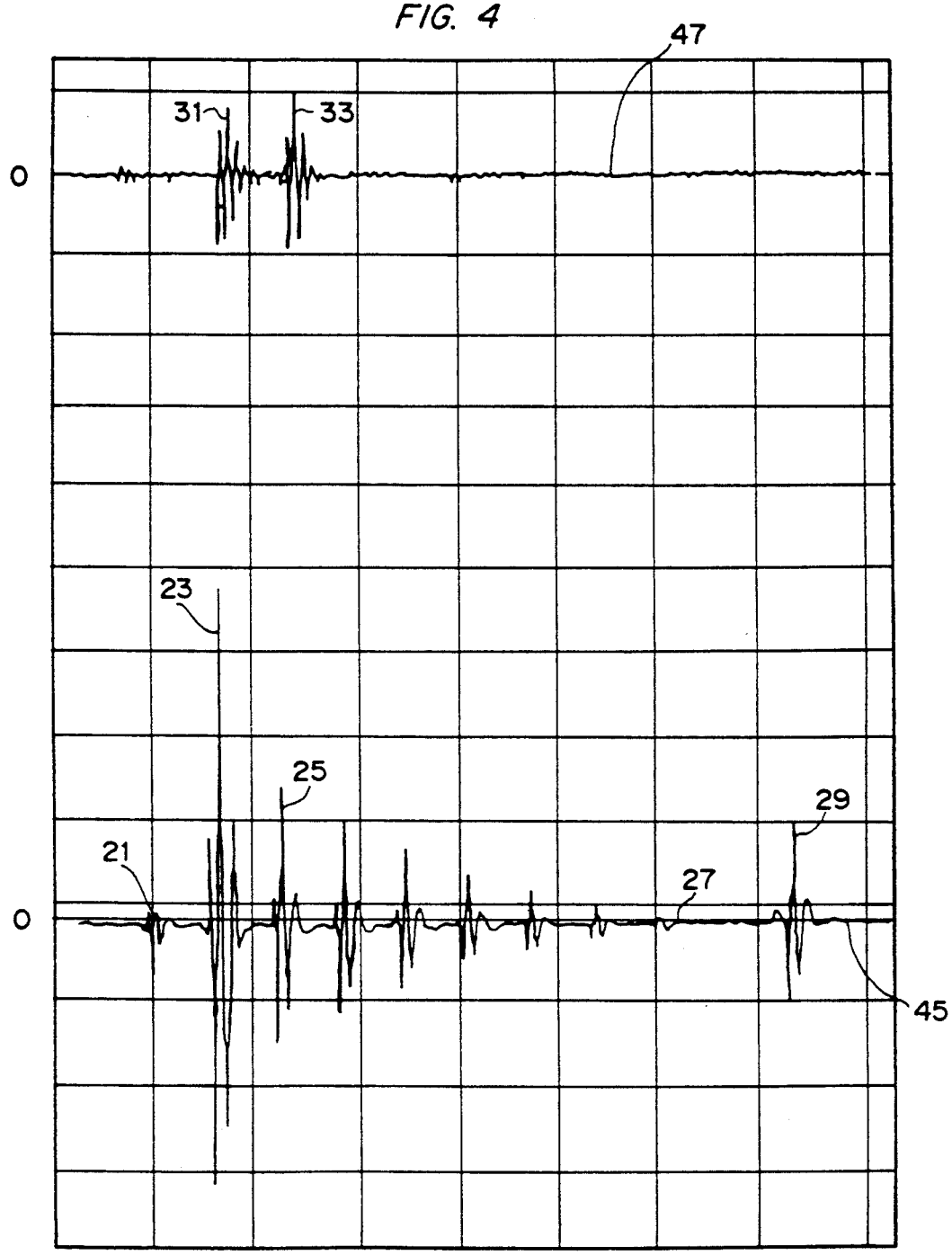
FIG. 4 shows the signals received from the flux leakage sensor and the variable reluctance sensor in response to the defects scanned in FIG. 3.

FIG. 4 shows the response of the flux leakage detector (lower trace 45) to all of the defects as a function of output voltage along the Y-axis vs. defect location along the X-axis. The output voltage varies as a function of the pit depth and diameter. Small hole 41 gives rise to a low-level transient 21. Large hole 43, pit depth 100% of the wall thickness, produces a very large transient 23. Transient 25, due to an 80% pit is somewhat lower in voltage level. Transient 27, due to the 20% pit is very small while the output level of a transient due to the 10% pit is nearly non-existent. Transient 29 (75% pit) is nearly as large as the level of transient 25 due to the 80% pit.

The upper trace 47 is the response of the variable reluctance sensor to the respective defects, however, the recording pen was shifted to the right relative to trace 45. It responds strongly to the two internal defects 41 and 43 to produce transients 31 and 33, but is otherwise featureless. The magnetic probe of this invention therefore provides means for detecting and discriminating between internal and external flaws in the wall of tubular goods.

FIGS. 5-8 are showings of the arrangement of the principal components of a presently-preferred embodiment of this invention and the presently-preferred mode of operation. FIG. 5 is a cross section along the axis of a pipe 10 in which a magnetic probe, generally shown as 11, is positioned. For simplicity, only the upper half of the probe is shown. However, it should be recognized that the device is symmetrical about the longitudinal axis.

Magnetic probe 11 consists of a central core 40 that is terminated at each end by pole pieces 42 and 44, all or part of which, such as portions 46 and 48, may be a prehensile material such as magnetic rubber. The prehensile pole pieces may be secured to central core 40 by any convenient means. Pole pieces 42 and 44 contain vent holes such as 43 and 45 to allow for the passage of the probe through fluids that may remain inside the pipe 10. Core 40, pole pieces 42 and 44 along with prehensile portions 46 and 48, comprise the second magnetizer. An eye 50, is provided to which a logging cable may be attached for drawing the probe along the interior of pipe 10. The rate of travel along a pipe during inspection is preferably about 125 feet per minute. For meaningful quantitative results, the probe must be drawn along the specimen at a constant velocity because the output voltage level is a function of the rate of change of the flux leakage vector.

A shoe, 52 is furnished which may be made of some non-magnetic substance such as K-monel metal. First magnetizer 26, which may be a bar magnet as shown or may be U-shaped, is mounted within a suitable cavity in shoe 52. Flux leakage sense coil 36 and variable reluctance sensor 38 are mounted in cells in shoe 52. Caliper arms 54 and 56 are provided, one end of each of which is pivoted from each end of shoe 52. The opposite ends of caliper arms 54 and 56 are slidingly seated in axial slots milled in core 40 as shown. One or more springs such as 58, radially expand shoe 52 and its sensors against the interior surface of pipe 10. The clearance between the sensors and the interior pipe wall, when the probe is in operation, is but a few thousandths of an inch.

FIG. 6 is an isometric view of shoe 52 showing the orientation of elongated flux leakage coil 36 which is aligned orthogonally to the longitudinal axis of pipe 10. The outer contour of shoe 52 may be curved to match the radius of curvature of the specimen to be inspected. Variable reluctance sensor 38 is shown embedded in a suitable cell. First magnetizer 26 is shown by dashed lines because it is not visible from the outer surface of shoe 52. A cable, 60, not shown in FIG. 5, conducts signals from the sensors to the outside world through a suitable logging cable of any well-known type.

FIG. 7 is a cross section along lines 7—7 of FIG. 5, showing the disposition of four shoes, 52, 52' 52" and 52"' around the internal circumference of pipe 10. At least four instrumented shoes are needed to monitor the full circumference of the pipe. If the areal coverage of the sector defined by each shoe is limited as shown, it may be necessary to provide at least two sets of four shoes each, with the sets being axially staggered with respect to each other to provide full circumferential coverage.

FIG. 8 is a schematic diagram of the electronic circuitry 61 for interfacing the output signals of the sensors with a logging cable. The output signals from the flux leakage coil and the variable reluctance sensor are fed to amplifiers 62 and 64 respectively. A potential of about 5 v is provided to activate the Hall-effect sensor. The amplifier outputs are coupled to a telemetry module 66 of any desired type where the analog signals from the sensors are digitized and serially delivered to a serial data output bus 68 for transmission via a logging cable to signal utilization equipment, not shown. Preferably the electronics module may be housed in the magnetic probe assembly itself in any convenient manner (not shown).

The best mode of operation has been included with the description of the presently-preferred embodiment. Many other designs may be conceived of by those skilled in the art but which will fall within the scope and spirit of this disclosure which is limited only be the appended claims.

What is claimed is:

1. A magnetic inspection probe for internal use for determining flaws in ferromagnetic tubular goods, comprising:

a first magnetizer element having poles of opposite polarity for establishing a magnetic circuit in a wall of a specimen under study, said wall having inner and outer surfaces;

a second magnetizer element having poles of opposite polarity for confining the magnetic field of the first magnetizer to a desired volumetric region in said wall;

said first magnetizer element being positioned between the poles of said second magnetizer element, like poles of said first and second magnetizer elements being juxtapositioned; and sensor means positioned between the poles of said first magnetizer for detecting and discriminating between flaws on the inner surface and flaws on the outer surface of said specimen.

2. The magnetic inspection probe as defined by claim 1 wherein:

said sensor means includes (a) means for measuring flux leakage from said wall, and (b) means for measuring the reluctance of said magnetic circuit.

3. The magnetic inspection probe as defined in claim 2, wherein:

the poles of said second magnetizer element include prehensile pole pieces secured thereto.

4. A magnetic inspection tool for detecting defects in small-diameter ferromagnetic tubular goods having inner and outer wall surfaces, comprising:

a first magnetizer element means for establishing a magnetic flux in a portion of the wall of a specimen under inspection;

a second magnetizer means for magnetically bottling said magnetic flux field within a desired volumetric region within said wall;

sensor means for detecting and discriminating between defects occurring on said inner and outer wall surfaces;

said second magnetizer element means including a central permanently magnetized core that is terminated at each end by a prehensile pole piece;

means for resiliently supporting said first magnetizer element from said central core;

said sensor means including a flux leakage sensor means and a sensor means for measuring the reluctance across the bottled magnetic flux field, both said sensor means being mounted adjacent said first magnetizer means on said first magnetizer supporting means; and means for radially expanding said means for resiliently supporting against the inner surface of said specimen.

5. The magnetic inspection probe as defined by claim 1 wherein:
said first and second magnetizer elements are permanent magnets.

6. The magnetic inspection tool as defined by claim 4, wherein:
said first and second magnetizers are permanent magnets.

* * * * *